United States Patent [19]
Dougherty

[11] Patent Number: 4,764,110
[45] Date of Patent: Aug. 16, 1988

[54] ORTHODONTIC FACE BOW

[76] Inventor: Harry L. Dougherty, 14434 Hamlin St., Suite 1, Van Nuys, Calif. 91401

[21] Appl. No.: 68,495

[22] Filed: Jul. 1, 1987

[51] Int. Cl.$^4$ .............................................. A61C 7/00
[52] U.S. Cl. ........................................... 433/5; 433/17
[58] Field of Search .............................. 433/5, 189, 17

[56] References Cited

U.S. PATENT DOCUMENTS

| | | | |
|---|---|---|---|
| 3,866,322 | 2/1975 | Broussard et al. | 433/5 |
| 4,087,915 | 5/1978 | Andrews | 433/5 |
| 4,212,637 | 7/1980 | Dougherty et al. | 433/5 |
| 4,445,853 | 5/1984 | Klein | 433/5 |
| 4,453,917 | 6/1984 | Nodai et al. | 433/5 |

Primary Examiner—Robert Peshock
Attorney, Agent, or Firm—Bruce L. Birchard

[57] ABSTRACT

An orthodontic face bow in which the outer bow is coupled firmly but separably to the inner bow by magnetic means and the inner bow is coupled to opposite molars in the mouth of the patient by a combination of mechanical and magnetic means, all to the end that, at a predetermined force the outer bow will separate from the inner bow and, at a higher force, the inner bow may be removed from the mouth of the patient so that prevention of injury to the patient by the inner bow may be prevented.

14 Claims, 1 Drawing Sheet

ORTHODONTIC FACE BOW

BACKGROUND OF THE INVENTION

1. Field of the Invention

This invention relates to dental appliances and more particularly to orthodontic face bows.

2. Prior Art

The most pertinent prior art is my U.S. Pat. No. 4,212,637, issued July 5, 1980 and entitled ORTHODONTIC FACE BOW. In that patent other prior art, particularly the patents issued to S. J. Kloehn are recited. As pointed out in my earlier patent, the Kloehn face bow and related dental appliances utilize a inner bow which is either welded to or otherwise affixed to the outer bow in a non-separable fashion. As a result, if a child grabs the outer bow of the appliance worn by his friend and pulls the outer bow forward to such an extent that the free ends of the inner bow of the device are completely removed from the mouth there is a distinct possibility that when the outer bow is released the elastic band which holds the entire appliance on the head will cause the pointed ends of the inner bow to strike the eye or eyes of the wearer of the bow and blindness can and has occurred.

In my earlier patent, I described and claimed an orthodontic face bow which included an externally applied outer bow and an internally applied inner bow which were mechanically coupled to each other but which were mechanically separable from each other in the event the outer bow was pulled. In one version a pair of pins which were welded to the inner bow were received by a pair of tubular sleeves supported from the outer bow in a position to receive and properly orient the inner bow. While this structure has represented a significant advance in the orthodontic face bow art, it is possible for the direction of the pulling to be such as to cause the pins to drag within the sleeves so that the separation does not occur when it should and, as a consequence, damage may occur.

Therefore, it is an object of this invention to overcome the disadvantages of the prior art devices.

It is a further object of this invention to provide a separable inner and outer bow structure for an orthodontic face bow in which separation of the inner and outer bows at a predetermined force level can be positively assured.

SUMMARY OF THE INVENTION

By intercoupling the inner and outer bows magnetically, the separation of the inner and outer bows at a predetermined force level can be positively assured. The use of ferro-ceramic magnets, which are small but have high magnetic field density, assures a firm interconnection of the inner and outer bows up to the force level at which failure to separate could cause serious injury to the wearer. Of course, other magnets, such as rubber-carried magnets may be used. The magnetic coupling concept is extended to the coupling of the inner bow to the molar tube which is associated with each of the molars on opposite sides of the mouth. The structure of the overall face bow is thus simplified and its cost to manufacturer is reduced.

BRIEF DESCRIPTION OF THE DRAWINGS

The features of the present invention which are believed to be novel are set forth with particularity in the appended claims. The present invention, both as to its organization and manner of operation, together with further objects and advantages thereof, may best be understood by reference to the following description taken in connection with the accompanying drawings, in which:

DESCRIPTION OF THE PREFERRED EMBODIMENT

Figure 1:
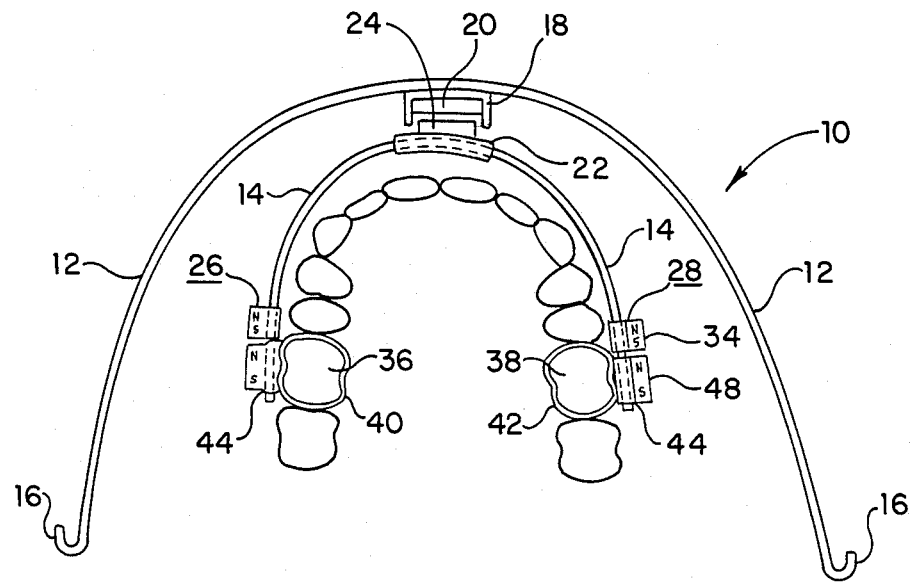
FIG. 1 is a plan view, partially schematic in nature, of an orthodontic face bow according to the present invention; and, FIG. 2 is a mechanical schematic diagram of a portion of the orthodontic face bow of FIG. 1.

In FIG. 1, orthodontic face bow 10 has an outer bow 12 and an inner bow 14. Outer bow 12 has hooks 16 at the extremities thereof for connection to an elastic band which traverses the back of the head of the patient or user.

Retainer 18, which is metallic in nature (and preferably non-magnetic in character) is welded or brazed to outer bow 12 and receives therein a bar magnet 20 of ferro-ceramic material or other magnetic material, which is polarized, as shown, or may be polarized in the direction of its thickness. Ceramic magnets produce high intensity magnetic fields and are light in weight. Magnet 20 may be secured to retainer 18 by means of modern-day adhesives which have great tensile strength.

A tube 22 of greater diameter than inner bow 14 is secured to inner bow 14 at its mid point. Magnet 24 is mounted on sleeve 22 by means of an adhesive, for example, and is polarized oppositely to bar magnet 20. Its length is such that is fits within the confines of retainer 18 and, in use, abuts bar magnet 20 with opposite poles contiguous so that bar magnet 24 is held firmly in position on bar magnet 20. Retainer 18 may be in the form of a box so as to confine the relative motion of the bar magnets 20 and 24, to two dimensions with the result that the relative motion of outer bow 12 and inner bow 14 is similarly confined. By choosing the flux density of the two bar magnets 20 and 24 the force necessary to separate outer bow 12 from inner bow 14 may be set at the desired level. It should be noted that with present sintering techniques, magnets 20 and 24 may take any shape. As a matter of fact, retainer 18 and magnet 20 may be a single mechanical-magnetic structure.

Figure 2:
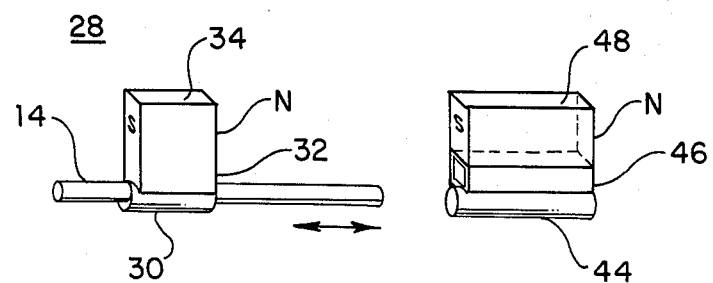

In addition to sleeve 22, inner bow 14 carries sleeve-stops 26 and 28. The construction of those sleeve-stops 26 and 28 is shown more clearly in FIG. 2. In FIG. 2, sleeve-stop 28 includes sleeve portion 30 which is welded or otherwise secured to inner bow 14. Sleeve-stop 26 carries another sleeve 30. A ceramic bar magnet 34 is secured to an adhesive, for example, to each sleeve 30 each magnet 34 being polarized as shown in FIG. 2.

Returning briefly to FIG. 1, left molar 36 and right molar 38 of the patient or user have molar bands 40 and 42, respectively, surrounding them. Each molar band has a molar tube 44 welded to it. The structure associated with each molar tube is shown, for graphical purposes, more clearly, in FIG. 2. The orientation of magnets 34 and 38 is shown, for graphical purposes, as normal to molar 38. Obviously this is the most uncomfortable orientation and, in practice, the magnets would be substantially parallel to molar 38.

In FIG. 2, molar tube 44 has welded thereto a rectangular tube 46 through which the teeth straightening wires pass. Ceramic bar magnet 48 is secured to rectangular tube 46 by means of an adhesive, such as the super-glues now widely available. If it is desired that ceramic bar magnet 48 be otherwise secured to rectangular tube 46, that bar magnet may be encased, except at its ends, in a non-magnet casing which may then be welded to rectangular tube 46.

The inside diameter of molar tube 44 is such as to receive inner bow 14 with a sliding fit.

In applying the orthodontic face bow according to this invention to the patient's mouth, after molar bands 40 and 42 and molar tubes 44 have been applied to the patient's left and right molars 36 and 38, respectively, the ends of inner bow 14 are inserted in the appropriate molar tubes and are slid into position, with stops 30 (which are tubular stops welded to inner bow 14), confronting the leading edge 50 of molar tube 44 (on both sides of the mouth) at which point inner bow 14 can slide no further into the mouth of the patient. The orientation and positioning of each bar magnet 34 is such that when sleeve 30 engages leading edge 50 of molar tube 44 one pole of bar magnet 34 is contiguous with the opposite pole of bar magnet 48 carried by molar tube 44. The force with which ceramic bar magnet 34 is held against ceramic bar magnet 48 can be predetermined by setting the magnetic flux density of the bar magnets in the course of their manufacture.

By using ceramic magnets the size of the magnets may be kept very small while achieving high levels of magnetic flux density (and thus, holding forces) up to any level that is desired. Ferro-ceramic materials are highly stable and resistant to oxidation and the fluids which may be found in the human mouth. Furthermore, the release that is provided by utilizing the bar magnets, particularly for the coupling of outer bow 12 to inner bow 14, assures that no injury will occur to the patient or user if another person pulls on the outer bow. The problems of prior art devices which resulted in eye injuries to the patient or user are thus totally eliminated. Mechanical clips which were utilized in my earlier orthodontic face bow, as described in U.S. Pat. No. 4,212,637, were more complex than the present design and were subject to all of the restrictions and failings of mechanical devices. Those problems are overcome with the orthodontic face bow according to the present invention. If one wishes to rely, alone, on the pressure of the neck strap, not shown, and the mechanical confinement produced by retainer 18, to keep outer bow 12 in position, magnets 20 and 24 may be positioned with their poles in the repulsion mode, i.e., N to N and S to S, in which case inner bow 14 will be forced inwardly towards stops 26, 28 and the pulling of outer bow 12 will have no tendency to pull inner bow 14 out of molar tubes 44, again preventing injury to the user.

While a particular embodiment of the present invention has been shown and described, it would be apparent to those skilled in the art that changes and modifications may be made therein without departing from this invention in its broader aspects, and it is the intention of the Claims which follow to cover all such changes and modifications as fall within the true spirit and scope of this invention.

I claim:

1. An orthodontic face bow including:
    inner bow means;
    outer bow means; and,
    magnetic coupling means including first magnetic means rigidly coupled to said outer bow means and second magnetic means rigidly coupled to said inner bow means;
    said first and second magnetic means being positioned, in the course of the use of said orthodontic face bow, contiguous with each other with a pole of a first polarity in said first magnetic means in conjunction with a pole of the opposite polarity in said second magnetic means, whereby said outer bow means is separable from said inner bow means when force is applied to said outer bow means in a direction outwardly from the wearer of said orthodontic face bow.

2. Apparatus according to claim 1 in which said first and second magnetic means each includes a ferro-ceramic magnet.

3. Apparatus according to claim 2 in which said ferro-ceramic magnets have predetermined magnetic flux densities, whereby the force for separation of said outer and inner bows is predetermined.

4. Apparatus according to claim 1 in which said inner bow has a pair of extremities and which includes, in addition:
    molar bands for connection each to one of the molar teeth on opposite sides of the wearer's mouth;
    molar tubes carried by said molar bands for receiving respective ones of said pair of extremities on said inner bow;
    stop means fixedly carried by said inner bow in the region of said extremities said stop means carrying thereon third magnetic means with fixed mechanical and magnetic-polar orientation;
    said molar tubes each carrying thereon fourth magnetic means with fixed mechanical and magnetic-polar orientation;
    said fixed mechanical and magnetic-polar orientation of said third magnetic means on said stop means and said fourth magnetic means carried by said molar tubes being such as to bring said respective magnetic means into mechanical conjunction with each other with their opposite magnetic poles contiguous, when said inner bow is in position with its opposite extremities passing thru respective ones of said molar tubes and said stop means engaging said molar tubes.

5. Apparatus according to claim 4 in which said third and fourth magnetic means each includes a ferro-ceramic magnet.

6. Apparatus according to claim 5 in which each of said ferro-ceramic magnets is a bar magnet.

7. Apparatus according to claim 2 in which each of said ferro-ceramic magnets is a bar magnet.

8. Apparatus according to claim 4 in which a rectangular tube is interposed between said molar tubes and said fourth magnetic means.

9. Apparatus according to claim 1 in which said first magnetic means includes a magnet-retainer having an inner dimension and carrying a first ferro-ceramic bar magnet therein with a fixed orientation and said second magnet means includes a second ferro-ceramic bar magnet having an outer dimension approximating said inner dimension of said magnet-retainer, whereby said second bar magnet may enter said magnet-retainer only with a predetermined orientation of said second bar magnet with respect to the orientation of said first bar magnet.

10. Apparatus according to claim 9 in which said magnet-retainer is U-shaped.

11. Apparatus according to claim 9 in which said magnet-retainer is box-shaped.

12. Apparatus according to claim 4 in which the mechanical force produced by said third magnetic means in conjunction with said fourth magnetic means exceeds the mechanical force produced by said first magnetic means in conjunction with said second magnetic means.

13. An orthodontic face bow including:
inner bow means;
outer bow means;
first magnetic means rigidly coupled to said outer bow means and second magnetic means rigidly coupled to said inner bow means;
said first and second magnetic means being positioned, in the course of the use of said orthodontic face bow, contiguous with each other, whereby said outer bow means is separable from said inner bow means when force is applied to said outer bow means in a direction outwardly from the wearer of said orthodontic face bow.

14. Apparatus according to claim 13 in which said first and second magnetic means, when contiguous, have like poles abutting.

* * * * *